(12) United States Patent
Hewig, III et al.

(10) Patent No.: US 11,293,930 B2
(45) Date of Patent: *Apr. 5, 2022

(54) METHOD FOR USING LIGHT SCATTERING IN REAL TIME TO DIRECTLY MONITOR AND CONTROL IMPURITY REMOVAL IN PURIFICATION PROCESSES

(71) Applicant: AMGEN INC., Thousand Oaks, CA (US)

(72) Inventors: Arthur C. Hewig, III, Newbury Park, CA (US); Duke H. Phan, Kenmore, WA (US); Yinges Yigzaw, Issaquah, WA (US); Robert Bailey, Bothell, WA (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/495,963

(22) Filed: Oct. 7, 2021

(65) Prior Publication Data

US 2022/0026442 A1 Jan. 27, 2022

Related U.S. Application Data

(63) Continuation of application No. 16/579,220, filed on Sep. 23, 2019, which is a continuation of application No. 13/850,664, filed on Mar. 26, 2013, now Pat. No. 10,481,164.

(60) Provisional application No. 61/799,742, filed on Mar. 15, 2013, provisional application No. 61/615,752, filed on Mar. 26, 2012.

(51) Int. Cl.
| | |
|---|---|
| *G01N 33/68* | (2006.01) |
| *C07K 16/00* | (2006.01) |
| *C07K 16/06* | (2006.01) |

(52) U.S. Cl.
CPC ......... *G01N 33/6854* (2013.01); *C07K 16/00* (2013.01); *C07K 16/065* (2013.01)

(58) Field of Classification Search
CPC ... G01N 33/6854; C07K 16/00; C07K 16/065
See application file for complete search history.

(56) References Cited

U.S. PATENT DOCUMENTS

| | | | |
|---|---|---|---|
| 6,635,224 B1 | 10/2003 | Gui et al. | |
| 7,416,698 B2 | 8/2008 | Smith et al. | |
| 10,481,164 B2* | 11/2019 | Hewig, III | C07K 16/065 |
| 2005/0014240 A1 | 1/2005 | Sherman et al. | |
| 2005/0240385 A1 | 10/2005 | Xie et al. | |
| 2007/0178013 A1* | 8/2007 | Kalonia | G01N 30/74 422/82.05 |
| 2008/0248059 A1 | 10/2008 | Capannoli et al. | |
| 2010/0022757 A1* | 1/2010 | Eon-Duval | A61P 35/00 530/387.3 |

FOREIGN PATENT DOCUMENTS

| | | |
|---|---|---|
| WO | 2005/114170 A1 | 12/2005 |
| WO | 2007/092827 A2 | 8/2007 |
| WO | 2009/018307 A2 | 2/2009 |
| WO | 2009/075764 A2 | 6/2009 |

OTHER PUBLICATIONS

Mhatre et al. "Determination of on-line differential refractive index and molecular weight via gradient HPLC interfaced with low-angle laser light scattering, ultraviolet, and refractive index detection" Analytical Chemistry (65(3)), pp. 283-266, 1994 (Year: 1994).*
Mhatre et al. "Characterization of proteins separated by displacement chromatography using low angle laser light scattering photometry" Chromatographia (38, No. 5/6), Mar. 1994, pp. 349-354 (Year: 1994).*
Harmann et al. "Characterization and analysis of thermal denaturation of antibodies by size exclusion high-performance liquid chromatography with quadruple detection" Analytical Biochemistry 325 (2004) 227-239 (Year: 2004).*
P.J. Wyatt, "Light scattering and the absolute charactization of macromolecules," Anal. Chim. Acta 272, 1-40 (1993).
B. H. Zimm, "The scattering of light and the radial distribution function of high polymer solutions," J. Chem. Phys. 16, 1093 (1948).
B. H. Zimm, "Apparatus and methods for measurement and interpretation of the angular variation of light scattering; Preliminary results on polystyrene solutions," J. Chem. Phys. 16, 1099-1116 (1948).
Mhatre et al. (1994). "Characterization of proteins separated by displacement chromatography using low angle laser light scattering photometry", *Chromatographia*, 38(5/6): 349-354.
Yigzaw et al. (Mar. 27, 2011). "Application of process analytical technologies (PAT) in biopharmaceutical chromatography processes", *Recent Advances in Biotechnology Product Development*, 241st ACS National Meeting, Anaheim, CA.

* cited by examiner

*Primary Examiner* — Daniel E Kolker
*Assistant Examiner* — James L Rogers
(74) *Attorney, Agent, or Firm* — Susan E. Lingenfelter (57) ABSTRACT

The invention provides a method for controlling contaminants in biopharmaceutical purification processes by using light scattering and UV absorbance to establish a determinant. The invention makes use of multi-angle light scattering (MALS) and UV as a continuous monitoring system to provide information about the elution peak fractions in real-time instead of conventional pooling methods that rely on a predetermined percent UV peak max value to initiate the pooling process; regardless of product quality.

4 Claims, 4 Drawing Sheets

METHOD FOR USING LIGHT SCATTERING IN REAL TIME TO DIRECTLY MONITOR AND CONTROL IMPURITY REMOVAL IN PURIFICATION PROCESSES

CROSS REFERENCE OF RELATED APPLICATION

This application is a continuation of application Ser. No. 16/579,220, filed Sep. 23, 2019, which is a continuation of application Ser. No. 13/850,664, filed Mar. 26, 2013, now U.S. Pat. No. 10,481,164, which claims the benefit of U.S. Provisional Patent Application Nos. 61/615,752, filed Mar. 26, 2012, entitled "A METHOD FOR USING LIGHT SCATTERING IN REAL TIME TO DIRECTLY MONITOR AND CONTROL IMPURITY REMOVAL IN PURIFICATION PROCESSES," and 61/799,742, filed Mar. 15, 2013, entitled "A METHOD FOR USING LIGHT SCATTERING IN REAL TIME TO DIRECTLY MONITOR AND CONTROL IMPURITY REMOVAL IN PURIFICATION PROCESSES," the entire contents of which are incorporated herein by reference.

FIELD OF INVENTION

The present invention relates to a method for in-line real-time monitoring of biopharmaceutical purification processes. These processes include chromatography, filtration, centrifugation, precipitation, and flocculation unit operations. This method uses real time information from light scattering in combination with absorbance or concentration to control the separation of a monomer protein from multimer species (dimer, oligomers, aggregates), lower molecular weight species (clips, etc) and other biological impurities.

BACKGROUND OF INVENTION

Cost pressures and ever increasing regulatory expectations require new thinking and approaches to development, manufacturing and release of drug substance and product. Efficient changeover between lots, real time disposition and assurance that product quality expectations are met are key features of the future of biologics. Quality by design (QbD) will be a key component of future analytical testing. The QbD paradigm focuses on the physiological importance of quality attributes for molecular design, process development, and control strategies. Analytical methodology will need to evolve and adapt to not only be able to monitor known biologically relevant quality attributes but also to have the flexibility to monitor new attributes as they are discovered without the need to continuously add new methods. A fundamental shift for process development will be to design quality into the product during development and manufacturing rather than relying solely on quality assessment at the end of production. Connecting process understanding with critical quality attributes (CQAs) and preventing issues in real time rather than troubleshooting them afterwards will minimize nonconformance issues and ensure product disposition. As such, the use of process analytical technologies (PAT) will be a key component to commercial manufacturing to monitor and control product quality during the manufacturing process and eliminate final release testing for some attributes.

There is a continuing need to develop methods for improving product quality and/or product analysis. Any improvement that increases product quality and decreases downstream process time can lead to reduced costs associated with manufacturing protein therapeutics. The invention fulfills these needs by providing a simple, effective method of controlling product separation as well as monitoring product quality by providing real time product analysis during biopharmaceutical purification processes thereby improving protein production.

SUMMARY OF THE INVENTION

The invention provides a method for determining a stop collection point during ion exchange chromatography comprising: applying a mixture containing a recombinant protein and biological impurities on to an ion exchange chromatography resin; selectively eluting the recombinant protein from the chromatography resin; monitoring the eluate with a laser light scattering detector and an UV absorbance detector; obtaining the signals from the light scattering detector and the UV absorbance detector and calculating a fraction LS/UV ratio for each fraction until the peak max LS/UV is determined; calculating a normalized LS/UV ratio for all subsequent fractions, wherein an increase in the normalized LS/UV ratio indicates an increase in the amount of biological impurities in the eluate pool; and terminating the elution when the normalized LS/UV ratio reaches a predetermined value.

In one embodiment the laser light scattering detector is a single or multiple angle light scattering detector.

In one embodiment the light scattering detector and UV absorbance detector are in series or parallel.

In one embodiment the eluate is continuously delivered to the UV absorbance detector, the laser light scattering detector, or both. In a related embodiment the entire eluate stream is delivered to the UV absorbance detector, the laser light scattering detector or both. In yet another related embodiment a sample of the eluate stream is diverted to the UV absorbance detector, the laser light scattering detector, or both, by a slipstream.

In one embodiment the normalized LS/UV ratio is calculated by dividing the fraction LS/UV ratio by the peak max LS/UV ratio.

In one embodiment the above method further comprises contacting the eluate with a next chromatography resin or processing step; and recovering the recombinant protein from the second chromatography resin or processing step. In a related embodiment the next chromatography resin is an affinity resin, an ion exchange resin, a hydrophobic interaction resin, a mixed modal resin, or a hydroxyapatite resin.

In one embodiment the recombinant protein is an antibody.

The invention also provides a recombinant protein purified by a process that separated the recombinant protein from biological impurities in a process stream using the above method.

The invention also provides a method for a determining the purity of a recombinant protein in the eluate pool from an ion exchange resin comprising: applying a mixture containing a recombinant protein and biological impurities on to an ion exchange chromatography resin; selectively eluting the recombinant protein from the chromatography resin; monitoring the eluate with a laser light scattering detector and an UV absorbance detector; obtaining the signals from the light scattering detector and the UV absorbance detector and calculating a fraction LS/UV ratio for each fraction until the peak max LS/UV is determined; calculating a normalized LS/UV ratio for all subsequent fractions, wherein an increase in the normalized LS/UV ratio indicates an increase of biological impurities in the eluate pool.

In one embodiment the laser light scattering detector is a single or multiple angle light scattering detector.

In one embodiment the light scattering detector and UV absorbance detector are in series or parallel.

In one embodiment the eluate is continuously delivered to the UV absorbance detector, the laser light scattering detector, or both In one embodiment the entire eluate stream is delivered to the UV absorbance detector, the laser light scattering detector or both. In a related embodiment the eluate stream is diverted to the UV absorbance detector, the laser light scattering detector, or both, by a slipstream.

In one embodiment the normalized LS/UV ratio is calculated by dividing the fraction LS/UV ratio by the peak max LS/UV ratio.

In one embodiment the method above further comprises contacting the eluate with a next chromatography resin or processing step; and recovering the recombinant protein from the second chromatography resin or processing step. In a related embodiment the next chromatography resin is an affinity resin, an ion exchange resin, a hydrophobic interaction resin, a mixed modal resin, or a hydroxyapatite resin.

In one embodiment the recombinant protein is an antibody.

The invention also provides a method for determining a stop collection point for ion exchange chromatography comprising: applying a mixture containing a recombinant protein and biological impurities on to an ion exchange chromatography resin; selectively eluting the recombinant protein from the chromatography resin; continuously determining the molar mass of the recombinant protein in the eluate; wherein an increase in the molar mass indicates an increase in the percentage of biological impurities in the eluate; and terminating the elution when the percentage of biological impurities in the eluate reaches a desired level.

In one embodiment the elution is terminated when the biological impurities reach a level of less than or equal to 5%.

In one embodiment the laser light scattering detector is a single or multiple angle light scattering detector.

In one embodiment the light scattering detector and UV absorbance detector are in series or parallel.

In one embodiment the eluate is continuously delivered to the UV absorbance detector, the laser light scattering detector, or both. In a related embodiment the entire eluate stream is delivered to the UV absorbance detector, the laser light scattering detector or both. In another related embodiment a sample of the eluate stream is diverted to the UV absorbance detector, the laser light scattering detector, or both, by a slipstream.

In one embodiment the method above further comprises contacting the eluate with a next chromatography resin or processing step; and recovering the recombinant protein from the second chromatography resin or processing step. In a related embodiment the next chromatography resin is an affinity resin, an ion exchange resin, a hydrophobic interaction resin, a mixed modal resin, or a hydroxyapatite resin.

In one embodiment the recombinant protein is an antibody.

The invention also provides a recombinant protein purified by a process that separated the recombinant protein from biological impurities in a process stream using the above method.

The invention also provides a method for a determining the purity of a recombinant protein in the eluate pool from an ion exchange resin comprising: applying a mixture containing a recombinant protein and biological impurities on to an ion exchange chromatography resin; selectively eluting the recombinant protein from the chromatography resin; continuously determining the molar mass of the recombinant protein in the eluate; wherein an increase in the molar mass indicates an increase in the percentage of impurities in the eluate pool.

In one embodiment the laser light scattering detector is a single or multiple angle light scattering detector.

In one embodiment the light scattering detector and UV absorbance detector are in series or parallel.

In one embodiment the eluate is continuously delivered to the UV absorbance detector, the laser light scattering detector, or both. In one related embodiment the entire eluate stream is delivered to the UV absorbance detector, the laser light scattering detector or both. In another related embodiment a sample of the eluate stream is diverted to the UV absorbance detector, the laser light scattering detector, or both, by a slipstream.

In one embodiment the method above further comprises contacting the eluate with a next chromatography resin or processing step; and recovering the recombinant protein from the second chromatography resin or processing step. In a related embodiment the next chromatography resin is an affinity resin, an ion exchange resin, a hydrophobic interaction resin, a mixed modal resin, or a hydroxyapatite resin.

OI one embodiment the recombinant protein is an antibody.

DETAILED DESCRIPTION OF THE INVENTION

Downstream purification processes play a key role in the production of biopharmaceuticals, and are developed to efficiently remove process and product related impurities. Some of the key impurities removed by downstream processes are high molecular weight species such as product dimers and larger order aggregate species. Typically the separation of the dimer and aggregate species from the protein product is challenging because the chemical makeup of these entities are quite similar and control of the purification process plays an important role in the selectivity, and therefore the purity, achieved. Traditionally separation of such entities is indirectly controlled using specific start and stop collection criteria derived from historical data. The reliance has been on ultraviolet spectroscopy at wavelengths near 280 nm to control these collection points. This is typically done by UV equipment integrated into lab development units and plant skid designs. Correlations between high molecular weight species removal with specific A280 readings, often based on specific UV absorbance measurements or percent of peak maximum, are determined during the development of the process. The primary deficiency with using absorbance measurements is that it is an indirect measurement of the product quality and relies heavily on historical development data. In addition, currently used methods base future purification process parameters on offline, post-elution, product quality analysis. The samples are taken after the elution pool has been collected and product quality is analyzed after the fact, taking days to weeks to complete. As such, changes to product quality are not detected before the end of a run when corrective actions or alternate strategies could have been employed to achieve a more desirable outcome. Without real time knowledge of the product quality, the user is required to adopt a conservative approach, establishing a stop collection at a point based on historical data, typically at some point somewhere before all harvestable product has been collected to avoid contamination by impurities and thereby decreasing the yield of product. Or the user can extend the parameters for collection to include an estimated amount of impurity contamination and subject the product to further purification steps, again resulting in decrease in product yield.

The present invention provides an alternative to such non-attribute specific methods by directly measuring, in real time, the product quality in a biopharmaceutical purification process stream to provide collection control point guidance and real time product quality analysis.

The invention is based on the discovery that collection control points in biopharmaceutical purification processes can be determined by monitoring the purity of a desired protein in a process stream in real time and use of that information to control the separation of a desired protein from biological impurities such as higher molecular weight multimer species (dimer, oligomers, aggregates), lower molecular weight species (clips, etc) and other biological impurities.

The invention provides a method for monitoring the purity of a protein in a process stream for use in collection control in biopharmaceutical purification processes by normalizing the light scattering signal from a multiangle laser light scattering device (MALS) with an absorbance signal (such as UV or refractive index detector (RI)). The method provides independently measuring the intensity of scattered light at different angles and different absorbance intensities. The ratio of the light scattering (LS) to absorbance concentration (for example, UV) is determined real time. The intensity of scattered light is proportional to the molecular mass of the monodisperse protein and its concentration. A monomeric protein peak, for instance, will have a constant ratio of LS/UV. Any deviation in that ratio signifies the product stream is contaminated with non-monomer impurities. When a purification process is operated in bind and elute or gradient elution the protein product is eluted first and aggregated species are present in the tail of the elution peak. Real time monitoring of the change in the ratio allows for a real time determination of the stop collection point based on the properties of the desired product at the time of elution, rather than using estimates and projections based on historical data and waiting for post-elution product analysis.

In one aspect the invention provides controlling cation exchange chromatography elution pooling and/or monitoring product quality based on a normalized LS/UV ratio as a determinant. During CEX elution, "fraction LS/UV ratios" are determined real-time for each elution fraction. A "peak max LS/UV ratio" is the ratio taken at the purest fraction; typically this is the peak max fraction. The normalized LS/UV ratio is obtained by dividing the instantaneous fraction LS/UV ratios of the elution peak by the value of pure max LS/UV ratio, the purest fraction of the elution peak. The real-time profile of the normalized LS/UV ratio across the elution peaks is calculated. An increase in the normalized LS/UV ratio indicates an increase in impurities in the eluate pool. The elution may be terminated when a predefined the target of normalized LS/UV ratio is achieved.

$$\text{Normalized } LS/UV = \left(\frac{\text{Fraction } LS/UV}{\text{Peak max } LS/UV}\right)$$

Figure 4:
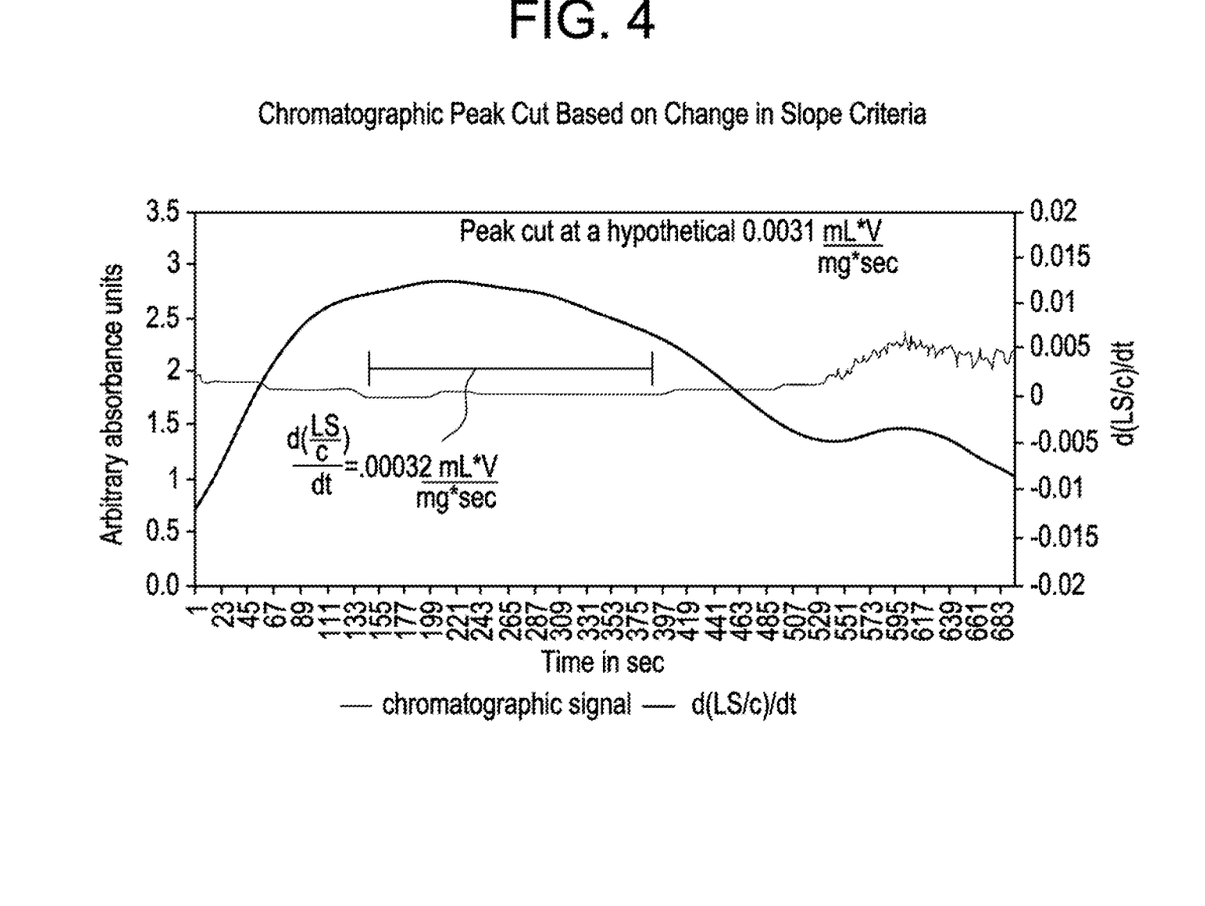
FIG. 4 how the slope of light scatter/concentration over time can be used to determine when to cut off collection of the peak. The left vertical axis plots absorbance, the right vertical axis plots the slope of light scattering/protein concentration and horizontal axis is Time in seconds. The read line is the chromatographic signal and the blue line is the slope of light scattering/protein scattering over time.

In another aspect the invention provides a method for monitoring and collection control. During the elution of a pure monomer, it is assumed that the solution will maintain a near-constant ratio between the light-scattering signal and the protein concentration (LS/c). The ratio can be calculated and monitored in real time using process control software and plotted as the instantaneous slope (d(LS/c)/dt). Empirically, the slope is near-zero during monomer elution, but remains constant. Changes in the slope correlate with elution of undesired species (i.e., positive deviations correlate with aggregate species); thus the slope can be used as a control value to automate main peak pooling as illustrated in FIG. 4.

In another aspect the invention provides a method for monitoring the purity of a protein in a process stream for use in collection control in biopharmaceutical purification processes by determining the change in the molar mass over time (dmm/dt) as a function of elution time. Process monitoring and control is accomplished by setting a specification related to the dmm/dt value. In one embodiment the dmm/dt would be a change of 500 g/mole/s.

Both of these methods eliminate the need for precise molar mass calculation of the desired protein.

The invention also provides monitoring the purity of a protein in a process stream for use in collection control in biopharmaceutical purification processes by real time determination of the molar mass or average molar mass of the material in a process stream. Any deviation in the molar mass signifies the product stream is contaminated with non-monomer impurities. This change in molar mass correlates to a change in the percentage of high molecular weight (HMW) impurities in the process stream. When the molar mass increases the % HMW increased and knowing the flow rate and the collection time, cumulative molar mass (cmm) can be calculated.

The change in molar mass (dmm/dt) as a function of % MMW (d % HMW/dmm) can be determined empirically. Combining d % HMW/dm with cumulative molar mass (cmm) gives you the % HMW the elution pool contains during the elution and in the final collection pool without having to perform post-elution analysis by SE-HPLC.

The molar mass of the material in the process stream can be determined using the light scattering signals collected by a MALS device and the concentration based on absorbance data, such as from UV or refractive index (RI).

The product concentration for use in determining the molar mass can be determined using Beer's Law:

$$A = \epsilon b c$$

where
A=Absorbance
b=path length
e=molar absorbitivity (Lmol$^{-1}$ cm$^{-1}$)
c=concentration of sample (molL$^{-1}$)

The determination of molar mass makes analysis is based on the Debye-Zimm equation:

$$(K^*c)/R(\theta,c)=1/(M_w P(\theta))+2A_2 c$$

where
R($\theta$,c) is the excess Rayleigh ratio of the solution as a function of scattering angle $\theta$ and concentration c, it is directly proportional to the intensity of the scattered light in excess of the light scattered by the pure solvent
c is the product concentration calculated above
$M_w$ is the weight-averaged solute molar mass
$A_2$ is the second virial coefficient in the virial expansion of the osmotic pressure
K* is the constant $4\pi^2(dn/dc)^2 n_0^2 1 N_a \pi_{o4}$
$N_a$ is Avogadro's number
P($\theta$) describes the angular dependence of the scattered light and can be related to the ms radius.

The analysis is based on the Debye-Zimm plot with additional constants to accommodate non-ideal behavior in the sample. (B. H. Zimm, "The scattering of light and the radial distribution function of high polymer solutions," J. Chem. Phys. 16, 1093 (1948); B. H. Zimm, "Apparatus and methods for measurement and interpretation of the angular variation of light scattering; Preliminary results on polystyrene solutions," J. Chem. Phys. 16, 1099-1116 (1948); P. J. Wyatt, Anal. Chim. Acta 272, 1-40 (1993)).

Computers or other such computational devices and other methods known in the art can be used to make the above calculations. Software is available commercially for determination of molar mass (for example ASTRA (Wyatt Technology Corp. Santa Barbara, Calif.)).

In one embodiment the percent increase in molar mass is less than or equal to 5%. In a preferred embodiment the percent increase in molar mass is less than or equal to 2%.

The methods of the invention can be used at: (a) the start of a purification process, for example to monitor the quality of material entering into the purification process for use as a feed-forward determinant to provide guidance during product collection and allowing predictability in the elution pool; (b) during the purification process itself to monitor the material being purified and as a stop collection signal for product elution in flow through mode, and (c) for monitoring and as a stop collection signal for the eluate from a bind and elute process. and the purity of an elution pool as it is collected.

The apparatus for light scattering and absorbance can be linked to or directly integrated into lab development units and plant skid designs to be in-line with the purification equipment and processes. The purification process stream can be analyzed in its entirety or via sampling either continuously, such as through a slip stream, or at regular intervals.

Laser light scattering systems are available commercially (Wyatt Technologies, Santa Barbara, Calif.; Kromatek, Essex, UK; Malvern Instruments, Worcestershire, UK).

Devices useful for measuring protein concentration are commercially available, such as refractive index and absorbance using UV (Optek, Carrollton, Tex.; Agilent, Santa Clara, Calif.; Waters, Milford, Mass.; GE Healthcare).

The laser light scattering system and the absorbance monitor can be connected in series or in parallel.

As used herein high molecular weight species (HMW) include proteinacous species having a higher molecular weight than the target protein mass, such as multimers. Multimers include everything other than the monomer of the target protein. For instance, a monomer of an IgG antibody encompasses the traditional tetrameric antibody composition comprising two identical, glycosylated heavy and light chains respectively. Multimers include proteinacous species having a higher molecular mass than the target protein mass, such as dimers (two identical proteins associated covalently or non-covalently) and aggregates (covalent or non-covalently associated whole and/or partial proteins).

Low molecular weight species (LMW) include proteinacous species having a lower molecular weight than the target protein mass, such as clips.

Biopharmaceutical purification processes include such unit operations that remove contaminants that change the molar mass, e.g. high molecular species, low molecular weight species and the like, including chromatography, filtration, centrifugation, precipitation, and flocculation.

During the purification of biopharmaceutical proteins, impurities including higher molecular weight species (dimer, oligomers, aggregates), lower molecular weight species (clips) and other biological impurities (host cell proteins, DNA, endotoxins, viral particles and process related contaminants and the like) are removed from the process stream. The purification techniques used must be scaleable, efficient, cost-effective, reliable, and meet the rigorous purity requirements of the final product. The invention provides a method of controlling product separation as well as monitoring product quality by providing real time product analysis during biopharmaceutical purification processes thereby improving protein production.

Typically, the first step of a downstream purification process involves clarification of the harvested cell culture broth where one or more of steps of precipitation, flocculation, filtration and/or centrifugation are used to separate the desired protein product from cells, cellular debris, and other biological contaminants. The inventive method can be used to monitor and control in real time the generation and collection of supernatant or filtrate from these processes. Methods of cell culture harvest are known to those skilled in the art (a reference or two). The desired protein may be precipitated away from non-proteinaceous polyanionic contaminants through the addition of neutral salts such as ammonium sulfate or potassium chloride, polymers such as PEG or dextran sulfate. Flocculation can be used to separate the desired product from cellular debris and other biological contaminants. Flocculents can be anionic or cationic polymers. Natural flocculents such as alginates or Chitosan; mineral flocculents such as colloidal clays and activated silica; and synthetic flocculents such as polyacrylamides and poly diallyldimethyammonium chloride can be used. Synthetic flocculents, manufactured to have specific molecular weights (based on chain length) and molecular distribution are also useful.

Separation of the desired protein from other cellular matter can be achieved by filtration using microfiltration, ultrafiltration, tangential flow filtration, alternating tangential flow filtration, for example (GE Healthcare; Refine Technologies, Hanover, N.J.).

Downstream purification processes also typically include one or more chromatographic separation steps such as affinity chromatography, ion-exchange, hydrophobic interaction, hydroxyapatite, chromatofocusing, gel filtration and reverse phase.

Affinity chromatography refers to the use of natural or synthetic compounds that specifically binds or interacts with a desired protein, such as an antibody, that is immobilized on a support or resin for the purpose of isolating, purifying, or removing the desired product. For the purification of antibodies, for example, affinity resins or supports include Protein A obtained from *Staphylococcus aureus*, Protein G from *Streptococcus* sp., Protein L from *Peptostreptococcus magnus*, and recombinant or synthetic versions or peptides of such. These resins include MAbSelect™, Amersham Biosciences, Upssala, Sweden; Prosep A®, Millipore, Billerica, Mass., among others.

Ion-exchange chromatography refers to chromatography for anion- or cation-exchange separation. Ion exchange resins that may be used in the invention include anion exchange resins and cation exchange resins. These include anionic exchange resins employing substituents such as diethylaminoethyl (DEAE), trimethylaminoethyl (TMAE), quaternary aminoethyl (QAE) and quaternary amine (O) groups, and cationic exchange employing substituents such as carboxymethyl (CM), sulfoethyl (SE), sulfopropyl (SP), phosphate (P) and sulfonate (S). Cellulosic ion exchange resins such as DE23, DE32, DE52, CM-23, CM-32 and CM-52 are available from Whatman Ltd. (Maidstone, Kent, U.K.) Sephadex-based and cross-linked ion exchangers are also useful. Examples include DEAE-, QAE-, CM-, and SP-Sephadex, and DEAE-, Q-, CM- and S-Sepharose, and Sepharose which are commercially available, for example, Amersham Biosciences, (Piscataway, N.J.). In addition, DEAE and CM derivatized ethylene glycol-methacrylate copolymer such as TOYOPEARL™ DEAE-650S and M and TOYOPEARL™ CM-650S or M are useful, Toso Haas Co., (Philadelphia, Pa.).

Various commercially available hydrophobic interaction chromatography (HIC) resins can also be used in the invention include resins comprising a base matrix (e.g., cross-linked agarose or synthetic copolymer material) to which hydrophobic ligands (e.g., alkyl or aryl groups) are coupled. Examples include Phenyl SEPHAROSE™ 6 FAST FLOW™; Phenyl SEPHAROSE™ High Performance; Octyl SEPHAROSE™ High Performance (Pharmacia LKB Biotechnology, AB, Sweden); Fractogel™ EMD Propyl or FRACTOGEL™ EMD Phenyl (E. Merck, Germany); MACRO-PREP™ Methyl or MACRO-PREP™ t-Butyl Supports (Bio-Rad, CA); WP HI-Propyl $(C_3)$™ (J. T. Baker, N.J.); and TOYOPEARL™ ether, phenyl or butyl (Toso-Haas, Pa.).

Downstream purification processes also include separating the desired product from viral contaminants. Various commercial filters are available, Plavona (Ashai, Glenview, Ill.) Viresolve (Millipore, Billerica, Mass.).

The present invention also finds use as a way to connect steps in the downstream purification process by providing a means for real time product analysis. Outflow or eluate from one process step can more easily move directly to the next step without delay for product analysis.

The present invention also finds use in the application of process analytical technology (PAT) to the process manufacturing environment. The invention is useful for analyzing and controlling a critical process parameter, such as the percent or ratio of impurities which affects a critical quality attribute the desired product, purity.

As used herein polypeptide monomer refers to a "peptide," "polypeptide" and "protein" which are used interchangeably throughout and refer to a molecule comprising two or more amino acid residues joined to each other by peptide bonds. Peptides, polypeptides and proteins are also inclusive of modifications including, but not limited to, glycosylation, lipid attachment, sulfation, gamma-carboxylation of glutamic acid residues, hydroxylation and ADP-ribosylation. Polypeptides can be of scientific or commercial interest, including protein-based drugs. Polypeptides include, among other things, antibodies, fusion proteins, and cytokines. Peptides, polypeptides and proteins are produced by cell lines using cell culture methods and may be referred to as "recombinant peptide", "recombinant polypeptide" and "recombinant protein". The expressed protein(s) may be produced intracellularly or secreted into the culture medium from which it can be recovered and/or collected.

Examples of polypeptides that can be purified with the methods of the invention include proteins comprising amino acid sequences identical to or substantially similar to all or part of one of the following proteins: tumor necrosis factor (TNF), flt3 ligand, erythropoeitin, thrombopoeitin, calcitonin, IL-2, angiopoietin-2, ligand for receptor activator of NF-kappa B (RANKL, tumor necrosis factor (TNF)-related apoptosis-inducing ligand (TRAIL), thymic stroma-derived lymphopoietin, granulocyte colony stimulating factor, granulocyte-macrophage colony stimulating factor (GM-CSF), epidermal growth factor, keratinocyte growth factor, megakaryote growth and development factor, RANTES, human fibrinogen-like 2 protein (FGL2) growth hormone, insulin, insulinotropin, insulin-like growth factors, parathyroid hormone, interferons including α-interferons, γ-interferon, and consensus interferons, nerve growth factor, brain-derived neurotrophic factor, synaptotagmin-like proteins (SLP 1-5), neurotrophin-3, glucagon, interleukins, colony stimulating factors, lymphotoxin-β, leukemia inhibitory factor, and oncostatin-M. Descriptions of proteins that can be purified according to the inventive methods may be found in, for example, *Human Cytokines: Handbook for Basic and Clinical Research, all volumes* (Aggarwal and Gutterman, eds. Blackwell Sciences, Cambridge, Mass., 1998); *Growth Factors: A Practical Approach* (McKay and Leigh, eds., Oxford University Press Inc., New York, 1993); and *The Cytokine Handbook, Vols. 1 and 2* (Thompson and Lotze eds., Academic Press, San Diego, Calif., 2003).

Additionally the methods of the invention would be useful to purify proteins comprising all or part of the amino acid sequence of a receptor for any of the above-mentioned proteins, an antagonist to such a receptor or any of the above-mentioned proteins, and/or proteins substantially similar to such receptors or antagonists. These receptors and antagonists include: both forms of tumor necrosis factor receptor (TNFR, referred to as p55 and p75), Interleukin-1 (IL-1) receptors (types I and II), IL-1 receptor antagonists, IL-1 antagonists or inhibitors, IL-2 receptors, IL-4 receptors, IL-15 receptors, IL-17 receptors, IL-18 receptors, Fc receptors, granulocyte-macrophage colony stimulating factor receptor, granulocyte colony stimulating factor receptor, receptors for oncostatin-M and leukemia inhibitory factor, receptor activator of NF-kappa B (RANK), osteoprotegerin, receptors for TRAIL (including TRAIL receptors 1, 2, 3, and 4), and receptors that comprise death domains, such as Fas or Apoptosis-Inducing Receptor (AIR).

Other proteins that can be purified using the invention include proteins comprising all or part of the amino acid sequences of differentiation antigens (referred to as CD proteins) or their ligands or proteins substantially similar to either of these. Such antigens are disclosed in *Leukocyte Typing VI (Proceedings of the VIth International Workshop and Conference*, Kishimoto, Kikutani et al., eds., Kobe, Japan, 1996). Similar CD proteins are disclosed in subsequent workshops. Examples of such antigens include CD22, CD27, CD30, CD39, CD40, and ligands thereto (CD27 ligand, CD30 ligand, etc.). Several of the CD antigens are members of the TNF receptor family, which also includes 41BB and OX40. The ligands are often members of the TNF family, as are 41BB ligand and OX40 ligand.

Enzymatically active proteins or their ligands can also be purified using the invention. Examples include proteins comprising all or part of one of the following proteins or their ligands or a protein substantially similar to one of these: a disintegrin and metalloproteinase domain family members including TNF-alpha Converting Enzyme, various kinases, glucocerebrosidase, superoxide dismutase, tissue plasminogen activator, Factor VIII, Factor IX, apolipoprotein E, apolipoprotein A-I, globins, an IL-2 antagonist, alpha-1 antitrypsin, ligands for any of the above-mentioned enzymes, and numerous other enzymes and their ligands.

The term "antibody" includes reference to both glycosylated and non-glycosylated immunoglobulins of any isotype or subclass or to an antigen-binding region thereof that competes with the intact antibody for specific binding, unless otherwise specified, including human, humanized, chimeric, multi-specific, monoclonal, polyclonal, and oligomers or antigen binding fragments thereof. Also included are proteins having an antigen binding fragment or region such as Fab, Fab', F(ab')$_2$, Fv, diabodies, Fd, dAb, maxibodies, single chain antibody molecules, complementarity determining region (CDR) fragments, scFv, diabodies, triabodies, tetrabodies and polypeptides that contain at least a portion of an immunoglobulin that is sufficient to confer specific antigen binding to a target polypeptide. The term "antibody" is inclusive of, but not limited to, those that are prepared, expressed, created or isolated by recombinant means, such as antibodies isolated from a host cell transfected to express the antibody.

Examples of antibodies include, but are not limited to, those that recognize any one or a combination of proteins including, but not limited to, the above-mentioned proteins and/or the following antigens: CD2, CD3, CD4, CD8, CD11a, CD14, CD18, CD20, CD22, CD23, CD25, CD33, CD40, CD44, CD52, CD80 (B7.1), CD86 (B7.2), CD147, IL-1α, IL-1β, IL-2, IL-3, IL-7, IL-4, IL-5, IL-8, IL-10, IL-2 receptor, IL-4 receptor, IL-6 receptor, IL-13 receptor, IL-18 receptor subunits, FGL2, PDGF-β and analogs thereof, VEGF, TGF, TGF-β2, TGF-β1, EGF receptor, VEGF receptor, hepatocyte growth factor, osteoprotegerin ligand, interferon gamma, B lymphocyte stimulator (BlyS, also known as BAFF, THANK, TALL-1, and zTNF4), C5 complement, IgE, tumor antigen CA125, tumor antigen MUC1, PEM antigen, LCG (which is a gene product that is expressed in association with lung cancer), HER-2, HER-3, a tumor-associated glycoprotein TAG-72, the SK-1 antigen, tumor-associated epitopes that are present in elevated levels in the sera of patients with colon and/or pancreatic cancer, cancer-associated epitopes or proteins expressed on breast, colon, squamous cell, prostate, pancreatic, lung, and/or kidney cancer cells and/or on melanoma, glioma, or neuroblastoma cells, the necrotic core of a tumor, integrin alpha 4 beta 7, the integrin VLA-4, B2 integrins, TRAIL receptors 1, 2, 3, and 4, RANK, RANK ligand, TNF-α, the adhesion molecule VAP-1, epithelial cell adhesion molecule (EpCAM), intercellular adhesion molecule-3 (ICAM-3), leukointegrin adhesin, the platelet glycoprotein gp IIb/IIIa, cardiac myosin heavy chain, parathyroid hormone, rNAPc2 (which is an inhibitor of factor VIIa-tissue factor), MHC I, carcinoembryonic antigen (CEA), alpha-fetoprotein (AFP), tumor necrosis factor (TNF), CTLA-4 (which is a cytotoxic T lymphocyte-associated antigen), Fc-γ-1 receptor, HLA-DR 10 beta, HLA-DR antigen, sclerostin, L-selectin, Respiratory Syncitial Virus, human immunodeficiency virus (HIV), hepatitis B virus (HBV), *Streptococcus mutans*, and *Staphylococcus aureus*. Specific examples of known antibodies which can be purified using the methods of the invention include but are not limited to adalimumab, bevacizumab, infliximab, abciximab, alemtuzumab, bapineuzumab, basiliximab, belimumab, briakinumab, canakinumab, certolizumab pegol, cetuximab, conatumumab, denosumab, eculizumab, gemtuzumab ozogamicin, golimumab, ibritumomab tiuxetan, labetuzumab, mapatumumab, matuzumab, mepolizumab, motavizumab, muromonab-CD3, natalizumab, nimotuzumab, ofatumumab, omalizumab, oregovomab, palivizumab, panitumumab, pemtumomab, pertuzumab, ranibizumab, rituximab, rovelizumab, tocilizumab, tositumomab, trastuzumab, ustekinumab, vedolizomab, zalutumumab, and zanolimumab.

The invention can also be used to purify recombinant fusion proteins comprising, for example, any of the above-mentioned proteins. For example, recombinant fusion proteins comprising one of the above-mentioned proteins plus a multimerization domain, such as a leucine zipper, a coiled coil, an Fc portion of an immunoglobulin, or a substantially similar protein, can be produced using the methods of the invention. Specifically included among such recombinant fusion proteins are proteins in which a portion of a receptor is fused to an Fc portion of an antibody such as etanercept (a p75 TNFR:Fc), and belatacept (CTLA4:Fc).

The methods of the invention can be used to purify recombinant proteins of interest. The expressed recombinant proteins may be produced intracellularly or be secreted into the culture medium from which they can be recovered and/or collected. In addition, the proteins can be purified, or partially purified, from such culture or component (e.g., from culture medium or cell extracts or bodily fluid) using known processes and products available from commercial vendors. The purified proteins can then be "formulated", meaning buffer exchanged, sterilized, bulk-packaged, and/or packaged for a final user. Suitable formulations for pharmaceutical compositions include those described in *Remington's Pharmaceutical Sciences*, 18th ed. 1995, Mack Publishing Company, Easton, Pa.

While the terminology used in this application is standard within the art, definitions of certain terms are provided herein to assure clarity and definiteness to the meaning of the claims. Units, prefixes, and symbols may be denoted in their SI accepted form. Numeric ranges recited herein are inclusive of the numbers defining the range and include and are supportive of each integer within the defined range. The section headings used herein are for organizational purposes only and are not to be construed as limiting the subject matter described. The methods and techniques described herein are generally performed according to conventional methods well known in the art and as described in various general and more specific references that are cited and discussed throughout the present specification unless otherwise indicated. See, e.g., Sambrook et al. Molecular Cloning: A Laboratory Manual, 3rd ed., Cold Spring Harbor Laboratory Press, Cold Spring Harbor, N.Y. (2001) and Ausubel et al., Current Protocols in Molecular Biology, Greene Publishing Associates (1992), and Harlow and Lane Antibodies: A Laboratory Manual Cold Spring Harbor Laboratory Press, Cold Spring Harbor, N.Y. (1990). All documents, or portions of documents, cited in this application, including but not limited to patents, patent applications, articles, books, and treatises, are hereby expressly incorporated by reference.

The present invention is not to be limited in scope by the specific embodiments described herein that are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

EXAMPLES

Example 1

This experiment was designed to investigate a method for controlling cation exchange chromatography elution pooling based on molar mass or dmm/dt as a determinant. The process made use of a combination of inline UV absorbance and multi-angle light scattering (MALS) for continuous real-time monitoring that enabled elution pooling based on molar mass purity, thereby controlling the contaminant content.

The clarified cell supernatant pool derived from a mammalian cell culture expressing a recombinant IgG in a 2000L bioreactor was loaded onto and eluted from a Mab SuRe (GE Healthcare) protein A column. The elution pool contained approximately 2,000-4000 g of IgG antibody of which approximately 10% was dimer, multimer, and aggregate mixture, and 2% low molecular weight (LMW) contaminants. The protein A eluent was loaded on a CEX column (Fractogel® SO3, (EDM Merck, Darmstadt, Germany) and was eluted with a salt gradient.

Undiluted and unconcentrated eluate from the column was diverted from the main processing outflow using a slipstream port and was continuously delivered to a AKTA UV-900 (GE Healthcare, Piscataway, N.J.) by an auxiliary 1100LC binary pump (Agilent Technologies Inc, Santa Clara, Calif.). The material then passed to a Heleos II (Wyatt Technology Incorporated, Santa Barbara, Calif.) light scattering detector. The sample was discarded after the readings. The signals were processed in real-time using a software program that calculated the molar mass across the elution peak using the signals from the light scattering detector and UV absorbance using the Debye-Zimm equation.

Figure 1:
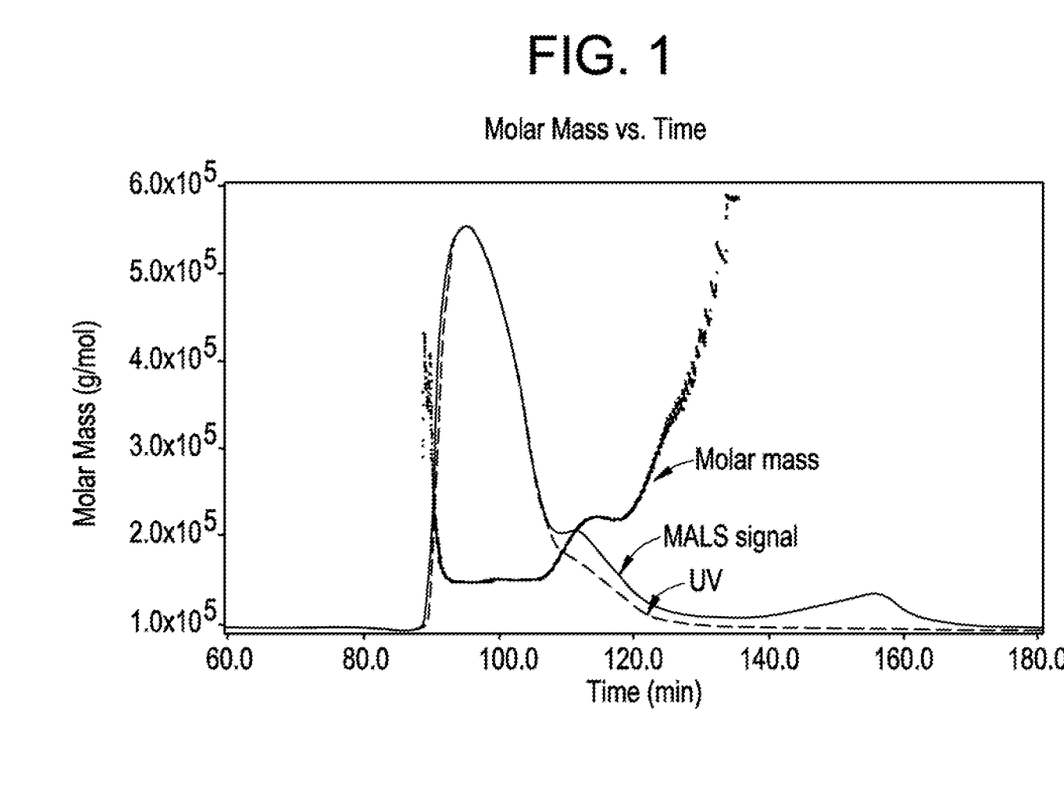
FIG. 1 indicates the elution profile of a typical monoclonal antibody from an ion-exchange column. The eluting protein profile is indicated with the UV absorbance reading and inline MALS signal. The real-time fraction molar mass profile shown is derived from the MALS and UV signal based on Debye-Zimm equation.

An increase in high molecular weight contaminants (HMW) in the elution was reflected in an increase in the average molar mass of the sample (see FIG. 1).

The stop collection point for the elution was set at a predetermined % HMW in the elution pool. As a comparison, the pooling was determined using % peak max at an absorbance of 300 nm and the % HMW of this control was determine by off-line size exclusion chromatography (SEC).

The results of five 2000 L runs is shown in Table 1. The peak collected using real time molar mass was as accurate, or more accurate, as the % peak max. The real time molar mass method had the advantage of not requiring the post-elution, off-line, product quality analysis and the product quality of the real time molar mass method was more consistent between lots.

TABLE 1

Comparison of elution peak collected using real time molar mass and peak max methods

| Run | % HMW in Elution Pool | |
|---|---|---|
| | Peak collection by Peak Max | Peak collection by Molar Mass |
| 1 | 1.8 | 2 |
| 2 | 3.6 | 0.6 |
| 3 | 2.1 | 2.1 |
| 4 | 1.5 | 2 |
| 5 | 0.6 | 1.9 |

Example 2

This experiment was designed to investigate a method for controlling cation exchange chromatography elution pooling based on a normalized LS/UV ratio as the determinant. The process made use of a combination of inline UV absorbance and multi-angle light scattering for continuous real-time monitoring that enabled elution pooling based on the change in the LS/UV ratio where the monomeric peak was expected to have a constant LS/UV ratio and any deviation in the LS/UV ratio indicated the presence of an impurity.

The clarified cell supernatant pool derived from a mammalian cell culture expressing a recombinant IgG in a 2000 L bioreactor was loaded onto and eluted from a Mab SuRe (GE Healthcare) protein A column. The elution pool contained approximately 2,000-4000 g of IgG antibody of which approximately 10% was dimer, multimer, and aggregate mixture, and 2% low molecular weight (LMW) contaminants. The protein A eluent was loaded on a CEX column (Fractogel® SO3, (EDM Merck, Darmstadt, Germany) and was eluted with a salt gradient.

Undiluted and unconcentrated eluate from the column was diverted from the main processing outflow using a slipstream port and was continuously delivered to a AKTA UV-900 (GE Healthcare, Piscataway, N.J.) by an auxiliary 1100LC binary pump (Agilent Technologies Inc, Santa Clara, Calif.). The material then passed to a Heleos II (Wyatt Technology Incorporated, Santa Barbara, Calif.) light scattering detector. The sample was discarded after the readings. The signals were processed in real-time using a software program that calculated the LS/UV ratio of the elution peaks, "fraction LS/UV ratio", using the signals from the light scattering detector and UV absorbance. In this example the purest fraction was the peak max. The stop collection point for the elution was set at a predetermined normalized LS/UV ratio in the elution pool.

As a comparison, the pooling was also determined using % peak max at an absorbance of 300 nm and the % HMW of this control was determine by off-line size exclusion chromatography (SEC).

Figure 2:
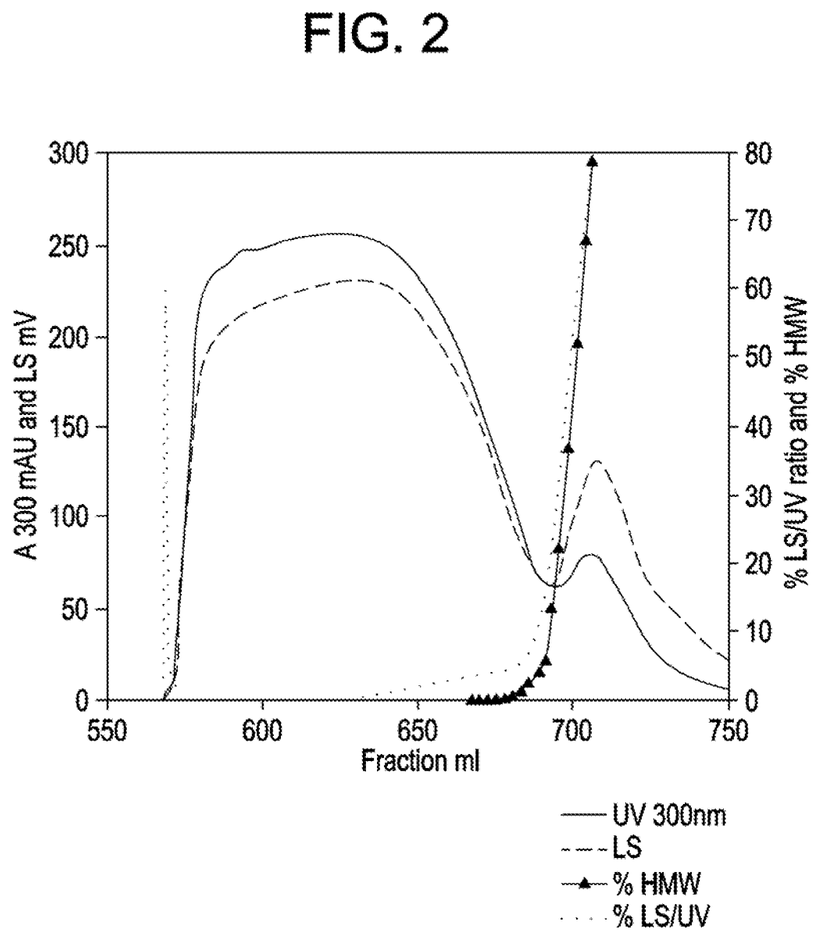
FIG. 2: Purity of a cation exchange elution peak as measured by offline SEC and real time LS/UV ratio calculation. Solid line-UV 300 nm. Dashed line-LS. Solid line with solid triangles-% HMW. Dotted line % LS/UV.

An increase in high molecular weight contaminants in the elution was reflected in an increase in the normalized LS/UV ratio. Purity of a cation exchange elution peak as measured by offline SEC and real time LS/UV ratio calculation is shown in FIG. 2. The figure shows an identical trend between the two methods. The LS/UV ratio was normalized and converted to % LS/UV to have the same Y-axis as the % HMW measured by SEC.

$$\% \ LS/UV = \left( \left( \frac{\text{Fraction } LS/UV \text{ ratio}}{\text{Peak max } LS/UV \text{ ratio}} \right) - 1 \right) \times 100$$

Figure 3:
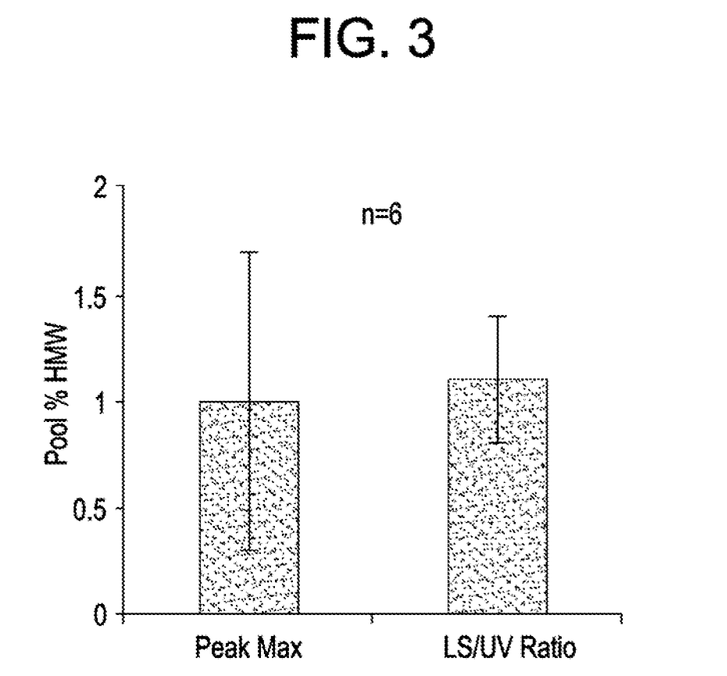
FIG. 3: Comparison of elution pool purity consistency between standard peak max based peak pooling and real time LS/UV ratio based peak pooling.

The results of six 2000 L runs are shown in FIG. 3. The peak collected using real time LS/UV was more consistent than % peak max based collection. The real time LS/UV method had the advantage of not requiring the post-elution, off-line, product quality analysis and the product quality of the real time LS/UV method was more consistent between lots.

What is claimed is:

1. A method for purifying a recombinant protein comprising:
    loading a mixture containing a recombinant protein and biological impurities on to a cation exchange chromatography resin;
    eluting by a salt gradient the recombinant protein from the cation exchange chromatography resin;
    measuring the intensity of light scattered by the eluate with a laser light scattering detector to obtain a light scattering (LS) signal;
    measuring the absorbance of the eluate with an ultraviolet (UV) absorbance detector to obtain an absorbance signal;
    calculating a ratio of the LS signal to the absorbance signal for each elution fraction to obtain a LS/UV fraction ratio;
    monitoring in real time during the elution of the recombinant protein the LS/UV fraction ratio over time for each elution fraction, wherein an increase in the LS/UV fraction ratio over time indicates an increase in the levels of biological impurities in the elution pool;
    terminating the elution when an increase in the LS/UV fraction ratio over time is detected; and
    recovering the recombinant protein from the eluate.

2. The method of claim 1, wherein recovering the recombinant protein in the eluate further comprises contacting the eluate with a second chromatography resin or processing step; and recovering the recombinant protein from the second chromatography resin or processing step.

3. The method of claim 1, wherein the recombinant protein is selected from the group consisting of a human antibody, a humanized antibody, a chimeric antibody, a recombinant fusion protein, or a cytokine.

4. The method of claim 1, wherein the recombinant protein is denosumab.

* * * * *